(12) United States Patent
Vaidya

(10) Patent No.: US 7,858,379 B2
(45) Date of Patent: Dec. 28, 2010

(54) APPARATUS AND METHOD FOR DETERMINING THE CONCENTRATION OF IODINE-CONTAINING ORGANIC COMPOUNDS IN AN AQUEOUS SOLUTION

(75) Inventor: Bikas Vaidya, College Station, TX (US)

(73) Assignee: Lynntech, Inc., College Station, TX (US)

( * ) Notice: Subject to any disclaimer, the term of this patent is extended or adjusted under 35 U.S.C. 154(b) by 283 days.

(21) Appl. No.: 12/132,265

(22) Filed: Jun. 3, 2008

(65) Prior Publication Data

US 2009/0017549 A1 Jan. 15, 2009

Related U.S. Application Data

(60) Provisional application No. 60/942,142, filed on Jun. 5, 2007.

(51) Int. Cl.
*G01N 33/00* (2006.01)

(52) U.S. Cl. .................. 436/125; 436/124; 436/126; 436/164; 436/169; 436/177

(58) Field of Classification Search .......... 436/124–126, 436/164, 169, 177
See application file for complete search history.

(56) References Cited

U.S. PATENT DOCUMENTS

| | | | | |
|---|---|---|---|---|
| 3,966,413 | A | * | 6/1976 | Marinenko .................... 422/81 |
| 4,049,382 | A | * | 9/1977 | Ross et al. ................... 205/780 |
| 5,300,442 | A | * | 4/1994 | Frant ........................ 205/778.5 |
| 6,627,450 | B1 | * | 9/2003 | Taylor et al. ................ 436/125 |

OTHER PUBLICATIONS

Johansen, G. et al, Talanta 1996, 43, 951-955.*
Farthing, D. et al, Journal of Chromatography B 2005, 826, 267-272.*
Arena, Matteo P. et al. "Rapid, Specific Determination of Iodine and Iodide by Combined Solid-Phase Extraction/Diffuse Reflectance Spectroscopy", Microanalytical Instrumentation Center, Iowa State University, Analytical Chemistry, vol. 74, No. 1, Jan. 1, 2002, pp. 185-190.
Argawal, Omi et al. A Sensitive Colorimetric Method for the Micro Determination of Iodine in Marine Water:, Elsevier Talanta, School of Studies in Chemistry, Pt. Ravishankar Shukla University, India, Talanta 49 (1999), pp. 923-928.

* cited by examiner

*Primary Examiner*—Arlen Soderquist
(74) *Attorney, Agent, or Firm*—Jeffrey L. Streets; Streets & Steele

(57) ABSTRACT

A method for determining the amount of a known iodine-containing organic compound in an aqueous solution. The method comprises electrochemically reducing the known iodine-containing organic compound in an aqueous medium to release iodide anions, chemically oxidizing the iodide anions to produce molecular iodine, and measuring the amount of molecular iodine. The known iodine-containing organic compound is preferably an aryl iodide, such as Iothalamate. Other preferred iodine-containing organic compounds include various glomerular filtration rate (GFR) marker compounds in plasma or urine samples, as useful in the measurement of GFR for an animal. The electrochemical reduction of the known iodine-containing organic compound is preferably performed in an electrochemical cell including a working electrode separated from a counter electrode by a cation exchange membrane. The working electrode most preferably includes bismuth and the counter electrode most preferably includes platinum.

27 Claims, 11 Drawing Sheets

APPARATUS AND METHOD FOR DETERMINING THE CONCENTRATION OF IODINE-CONTAINING ORGANIC COMPOUNDS IN AN AQUEOUS SOLUTION

CROSS-REFERENCE TO RELATED APPLICATIONS

This application claims the benefit of U.S. provisional patent application 60/942,142, filed on Jun. 5, 2007.

This invention was made with government support under grant number 1 R43 DK 071370-01 awarded by the Department of Health and Human Services (NIDDK). The government has certain rights in this invention.

BACKGROUND OF THE INVENTION

1. Field of the Invention

The present invention relates to apparatus and methods for measuring the concentration of iodine-containing compounds in an aqueous solution, such as in plasma or urine.

2. Background of the Related Art

Chronic kidney disease (CKD) is a major medical problem in the United States and the rest of the world. According to the National Kidney Foundation in the U.S. alone 20 million Americans have CKD and at least 20 million more are at risk. Over the next 10 years, the number of patients in the U.S. with kidney failure (end stage renal disease, ESRD) is expected to double. By 2010, the cost of ESRD may exceed $28 billion annually, according to the United States Renal Data System, Bethesda, Md.

Some major causes of kidney dysfunction include hypertension, diabetes, lupus erythematosus, chemotherapy and immuno-suppression therapy. In all these instances, it is essential to have an accurate test of kidney function to determine the most appropriate therapeutic intervention, because preventing or slowing the progression of renal disease through early recognition of impaired renal function can reduce the number of patients with end-stage renal disease. At the same time, accurate testing of kidney function can prevent or reduce the need for dialysis and kidney transplantation, both of which are costly procedures.

Glomerular Filtration Rate (GFR) is an accepted measure of how well the kidneys are removing wastes and excess fluid from the blood. A person's current GFR can be determined by administering certain agents into the blood and then measuring their disappearance from the blood and their appearance in urine. Accordingly, GFR is a direct measurement of kidney function and the value of an individual's GFR has been shown to drop before the onset of symptoms of kidney failure. A decrease in GFR correlates with the pathologic severity of kidney disease. Replacement therapy with dialysis or transplantation is presently considered to be necessary when the GFR decreases below 15 mL/min/1.73 m$^2$ The level of GFR is the product of the single nephron glomerular filtration rate (SNGFR) multiplied by the number of functioning nephrons (N) in both kidneys, as set out in Equation (1).

$$GFR = N \times SNGFR \quad \text{Equation (1)}$$

the level of GFR can be decreased either because of reduced nephron number (as in CKD) or because of a reduction in SNGFR (caused by physiologic or pharmacologic alterations in glomerular hemodynamics). There are several factors that affect GFR, including kidney disease, pregnancy, reduced kidney perfusion, marked increase or deficit of extracellular fluid volume, nonsteroidal anti-inflammatory drug use, acute protein load and habitual protein intake, blood glucose control (in diabetic patients), arterial blood pressure and the use of certain classes of antihypertensive agents.

GFR is estimated from the urinary clearance of an ideal filtration marker, defined by Equation (2).

$$C_i = (U_i \times V)/P_i \quad \text{Equation (2)}$$

In this equation, $C_i$ is the clearance of the ideal filtration marker (i), $U_i$ is the urinary concentration of (i), V is the urine flow rate, and $P_i$ is the average plasma concentration of (i) during the time interval of urine collection. If substance (i) is freely filtered across the capillary wall and neither secreted nor reabsorbed, then $C_i$=GFR.

Inulin fulfills the criteria as an ideal filtration marker, and its urinary clearance has long been considered the "gold standard" in measuring GFR. Normal values for inulin clearance in young men and women are approximately 130 and 125 mL/min/1.73 m$^2$, respectively. These values decline with age by approximately 10 mL/min/1.73 m$^2$ per decade after 30 to 40 years of age.

Although inulin is considered to be the ideal filtration marker, its availability is limited and the protocols for measurement of inulin clearance are inconvenient. Clearance of endogenous filtration markers, such as creatinine and urea, has also been used to assess GFR. Serum creatinine determination has become a mainstay in the standard laboratory profile of renal function because of its convenience and low cost. Nevertheless, serum creatinine remains a crude marker of GFR. Creatinine concentrations are insensitive to detection of mild to moderate reductions in GFR. This is due to the nonlinear relation between concentrations of creatinine in blood and GFR. Use of the serum creatinine level as an index of GFR rests on three important assumptions: (1) creatinine is an ideal filtration marker whose clearance approximates GFR, (2) creatinine excretion rate is constant among persons and over time, and (3) measurement of serum creatinine is accurate and reproducible across clinical laboratories. Although serum creatinine concentration can provide a rough index of the level of GFR, none of these assumptions is strictly true, and numerous factors, such as kidney disease, reduced muscle mass, ingestion of cooked meat, and malnutrition, can lead to errors in estimating the level of GFR from the serum creatinine concentration. In addition, several substances such as, glucose, uric acid, ketones, plasma proteins and cephalosporin may lead to falsely high creatinine values when the Jaffe calorimetric method is used.

Alternative clearance methods that use exogenous filtration markers, such as I-125 Iothalamate sodium, Tc-99m DPTA and Cr-51-EDTA, are simpler and have been used in clinical trials. However, they are inconvenient and expensive because of the use of radioactive material and the need for trained personnel to perform the procedure. Additionally, the use of a radioactive marker is also compromised by the short shelf-life of the agent and a desire to avoid radiation exposure. Thus, there is a need to develop methods that can be used in clinical settings without use of a radioactive marker, yet provide precise estimates of GFR.

Iohexol and Iothalamate are iodinated radiographic contrast media developed for use in diagnostic radiology. Because they do not bind to protein and are totally excreted by the kidney through the process of glomerular filtration, their clearance from plasma after a single injection can be used to estimate GFR in humans. Several analytical methods have been developed for determination of Iohexol and Iothalamate concentrations in plasma and urine. The most commonly used procedures involve high performance liquid chromatography (HPLC) and capillary electrophoresis (CE), but both of these separation techniques are suitable for use only in a laboratory setting as both of the techniques require sophisticated instrumentation, regular maintenance and highly skilled personnel to run the tests.

Another simple clearance method is the X-ray fluorescence (XRF) measurement of iodine. XRF is convenient in its simplicity and capacity for rapid turnaround, which are important in the clinical settings. Drawbacks to the XRF method include high detection limits and relatively large sample requirements (4 to 6 mL of whole blood is recommended). Methods such as inductively coupled plasma-atomic emission spectroscopy (ICP-AES) for measurement of iodine can be used to determine Iohexol and Iothalamate concentrations, however, these methods require sophisticated instrumentation, regular maintenance and highly skilled personnel to run the tests.

SUMMARY OF THE INVENTION

The present invention provides a method of determining the amount of a known iodine-containing organic compound in an aqueous solution. The method comprises electrochemically reducing the known iodine-containing organic compound in an aqueous medium to release iodide anions, chemically oxidizing the iodide anions to produce molecular iodine, and measuring the amount of molecular iodine. The known iodine-containing organic compound is preferably an aryl iodide, such as Iothalamate. Other preferred iodine-containing organic compounds include various glomerular filtration rate (GFR) marker compounds.

The method is particularly useful in the measurement of a GFR marker compound in an aqueous solution that includes plasma or urine. Where the sample contains proteins, a majority of the protein is preferably removed from the aqueous solution prior to electrochemically reducing the known iodine-containing organic compound. Accordingly, the method may be used as an analytical tool that facilitates a quick and effective determination of GFR for an animal. Such a method may further include administering the iodine-containing organic compound into the body of an animal, periodically obtaining a sample the blood or urine of the animal during the period following administration of the iodine-containing organic compound, measuring the amount of iodine-containing organic compound in each sample obtained, and using the quantity of iodide determined for each sample to determine a glomerular filtration rate for the animal.

The electrochemical reduction of the known iodine-containing organic compound is preferably performed in an electrochemical cell including a working electrode separated from a counter electrode by a cation exchange membrane. The working electrode most preferably includes bismuth and the counter electrode most preferably includes platinum.

Following electrochemical reduction, the iodide anions are chemically oxidized with an oxidizing agent, such as an oxidizing agent selected from the group consisting of peroxymonosulfate, ozone, and combinations thereof. The released iodide anions are oxidized to form molecular iodine, preferably either by mixing an oxidizing agent into the aqueous medium containing the released iodide anions or by passing the aqueous medium with the released iodide anions through a filter pre-loaded with a powdered oxidant, such as peroxymonosulfate. The chemical oxidation is desirably performed in an airtight reaction vessel to avoid evaporative loss of gaseous molecular iodine.

In a preferred embodiment, the amount of molecular iodine is measured by extracting the iodine on a polyvinylpyrrolidone coated membrane to form an iodine-PVP complex, and then measuring the color of the iodine-PVP complex on the membrane. A reflectance absorbance measurement may be made using a spectrophotometer optionally coupled to an optical fiber probe including at least one illumination fiber and at least one read fiber. To facilitate the reflectance absorbance measurement, the polyvinylpyrrolidone is preferably coated on one side of the membrane and the membrane is poly(styrenedivinylbenzene), which is white and provides good adherence of the PVP.

DETAILED DESCRIPTION OF THE INVENTION

Figure 1:
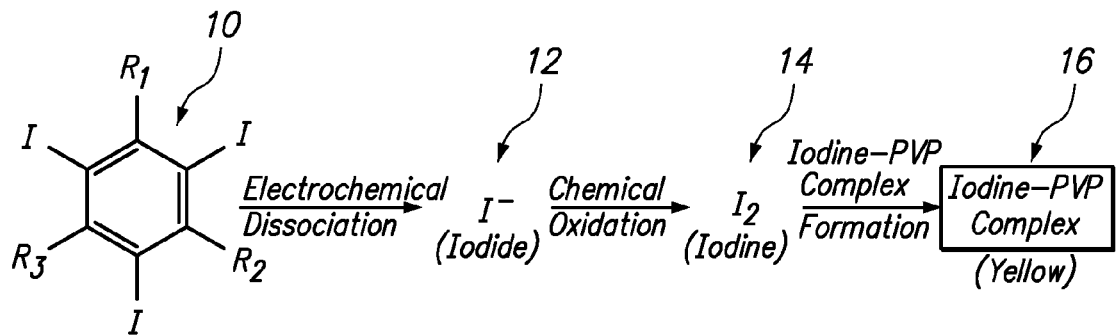
FIG. 1 is a flow diagram that summarizes the major steps of the foregoing process.

The present invention provides a method for determining the amount of a known iodine-containing organic compound in an aqueous solution. This method uses electrochemical reduction and dissociation of an iodine-containing organic compound, such as an aryl iodide, and chemical oxidation of iodide followed by selective calorimetric determination of the iodine for rapid determination of the amount of the iodine-containing organic compound. In this method, iodine-containing organic compounds 10 are electrochemically dissociated at a working electrode, optionally including bismuth or bismuth modified gold or carbon, in order to release iodine from the aryl iodide as free iodide. The electrochemically generated iodide 12 is then chemically oxidized to iodine 14, then the iodine is measured. In one embodiment, the iodine is filtered and passed through a polyvinyl pyrrolidone (PVP) coated membrane, such as poly(styrene divinylbenzene), where the iodine adsorbs onto the PVP and produces a yellow coloration. The iodine-PVP complex 16 is stable and also has a much higher extinction coefficient compared to molecular iodine. Quantification of the iodine adsorbed onto the PVP-coated membrane is achieved by measuring reflectance absorbance with an optical fiber probe and a spectrophotometer. FIG. 1 is a schematic flow diagram that summarizes the major steps of the foregoing process.

The present invention demonstrates the feasibility of using electrochemical dissociation of iodine-containing organic compounds to release iodine, chemical oxidation to form iodine, and calorimetric measurement of the iodine-PVP complex to determine the concentration of the iodine-containing organic compound in an aqueous solution, such as an aqueous solution include urine and plasma samples. Accordingly, it is now shown that (1) iodine from the aryl iodides is quantitatively released as free iodide upon electrochemical reduction, (2) iodine released from the aryl iodides can be determined quantitatively by a calorimetric method, and (3) the dynamic range and lower limit of detection of the aryl iodides in urine and in plasma samples is more than satisfactory. Optionally, the iodide-containing organic compound may be used as a GFR marker compound to measure kidney clearance, a radio contrast agent for imaging, or a dual-use component capable of serving multiple purposes. For example, a radio contrast agent may be used for the purpose of imaging, but the elimination of the agent by the kidneys can be monitored in order to determine the GFR without administering any additional agents.

The electrochemical reduction of an iodine-containing organic compound, such as the aryl iodide compound referred to as Iothalamate, to release iodide can be achieved by careful selection of electrode material and special design of electrochemical cell. For electrochemical reduction of the iodine-containing organic compound, a mercury working electrode or a bismuth working electrodes can be used because these electrode materials have relatively high over-potentials for hydrogen reduction. The high over-potentials of these electrode materials allows application of negative enough potential in aqueous medium to reduce aryl iodide with very little or no break down of the solvent. Even though mercury has a higher over-potential for hydrogen reduction than does bismuth, a bismuth electrode is preferred because of toxicity and disposal problems associated with mercury and mercury compounds.

In one embodiment, two compartments of an electrochemical cell are separated by a Nafion membrane in order to prevent the iodide produced by the electrochemical reduction of aryl iodide at the bismuth working electrode (at a relatively high negative potential) from being subsequently oxidized at a platinum counter electrode to iodine and then escaping from the cell as gaseous iodine. A first compartment of the cell contains the working electrode and the second compartment contains a platinum counter electrode. Optionally, a Ag/AgCl reference electrode may also be disposed in the second compartment. The Nafion membrane separating the two compartments allows charge transfer (proton exchange), but it repels all anionic species because of its negatively charged surface. Therefore, the membrane prevents anions, including iodide, from entering the second compartment.

The electrolyzed sample is transferred into an air tight container, such as a syringe, then contacted with a chemical oxidant having an oxidation potential greater than iodine, such as ozone or peroxymonosulfate (such as that available from DuPont of Wilmington, Del., under the trademark Oxone). The iodide anions released from the iodine-containing organic compound will be chemically oxidized to molecular iodine. For example, the electrolyzed sample may be forced through a filter pre-loaded with Oxone powder. Alternatively, a liquid oxidant solution, such as an Oxone solution, may be mixed with the sample to convert the iodide to iodine.

The amount of iodine in the resulting solution is then measured. These measurements may involve the a step such as adding starch into the iodine solution, adding leucocrystal violet into the iodine solution, measuring the direct ultraviolet absorption of iodine, or titrating the iodine with sodium thiosulfate. However, in a preferred embodiment, the resulting iodine-containing solution is passed through a PVP-coated solid phase extraction (SPE) membrane (such as poly(styrenedivinylbenzene)). Because of its hydrophobicity, molecular iodine will be quantitatively extracted from water as an iodine-PVP complex upon passing an aqueous iodine sample through the PVP coated polymeric membrane. The resulting PVP-iodine complex is less volatile and more intensely colored than molecular iodine. When passed through the PVP coated membrane, the iodine-containing solution will adsorb as an iodine-PVP complex only on the top coated surface of the membrane resulting in a very high sensitivity for the calorimetric detection of iodine. The yellow color developed by the formation of iodine-PV complex on the PVP-coated membranes can be very easily measured using an inexpensive and commercially available reflectance spectrophotometer.

An additional advantage of this approach is that the measurement of the iodine-containing organic compound is not affected by other sources of iodide or iodine, such as iodinated salt ingested by the patient, or even yellow colored substances that may be present in urine. Colored substances may not even stick to the sensing membrane, but even if they do adsorb to the membrane they can be subtracted out from the total iodine measured. Accordingly, a background spectrum of the free iodine or iodine present in the sample prior to the electrochemical reduction of the sample is similarly measured and subtracted out from the total iodine measured. Because the amount of iodide found in plasma and urine both are well below 1 ppm, this correction may not even be required in most cases.

Figure 2:
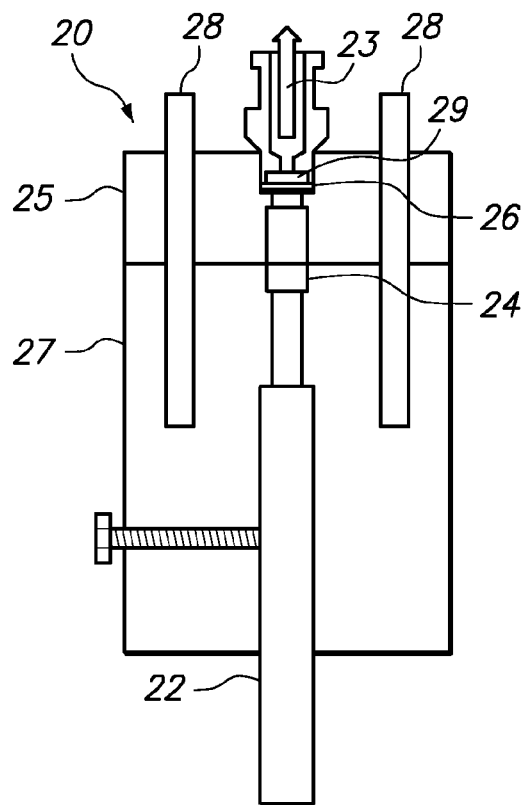
FIG. 2 is a diagram of an optical detection system for determining iodine-PVP concentration by measuring the spectral difference in the light reflected from a sensing membrane.

FIG. 2 is a diagram of an optical detection system 20 for performing reflectance absorbance spectroscopy of the iodine-PVP complex. The optical detection system 20 includes an Ocean Optics S2000 miniature fiber optic spectrophotometer equipped with a pulsed xenon lamp (not shown in the figure) and a reflection/backscattering probe consisting of a tight bundle of seven (7) optical fibers in a stainless steel ferrule 22. The seven optical fibers include six illumination fibers around one read fiber. Light from the six illumination fibers around the outside is focused by the double convex lens 24 onto the PVP-coated sensing membrane. The light reflected off the PVP membrane passes through the lens and returns down the center fiber to the spectrometer.

Figure 3:
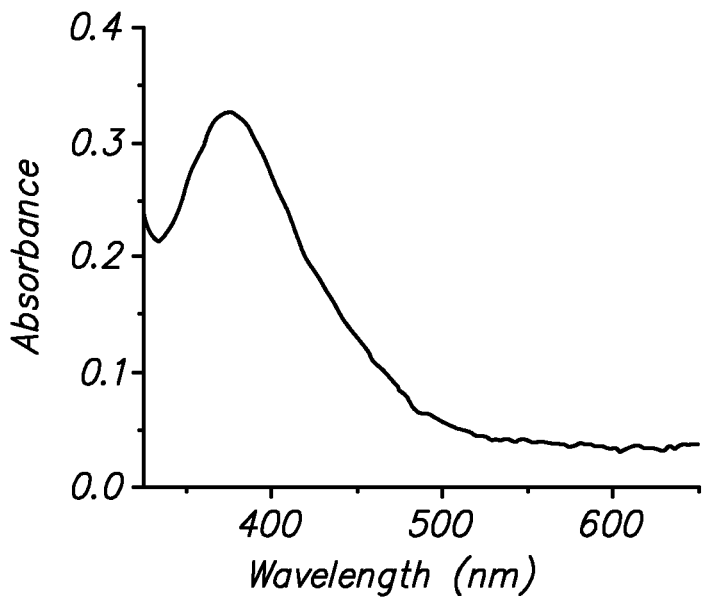
FIG. 3 is a graph of a reflectance absorbance spectrum obtained from a sample with 10 ppm iodine using the optical detection system shown in FIG. 2.

The top detachable portion 25 of the optical detection system is designed to serve as a fluidic channel 23 through which to pass the test sample containing iodine during oxidation, and to hold the sensing membrane 26 in place (at the focal plane) for reflectance absorbance spectroscopy during optical detection. For optical measurement, the top detachable portion 25 with the PVP coated sensing membrane 26 is assembled as shown in FIG. 2, with the top portion 25 and lower portion 27 aligned by pins 28, and the reference spectrum/base line recorded. The top portion is then pulled out and an aliquot (typically 200 μL) of iodine sample solution pulled through the PVP coated membrane 26, supported by a frit 29, using a vacuum pump (not shown). During this process iodine from the sample solution is adsorbed on the PVP coated membrane 26 as a yellow colored iodine-PVP complex. The top portion 25 is placed back onto the lower portion 27 including the optical detection system as before and the reflectance absorbance spectrum taken and the amount of iodine present in the sample calculated. FIG. 3 is a graph of the reflectance absorbance spectrum obtained from a sample with 10 ppm iodine using the optical detection system shown in FIG. 2. The graph shows a strong absorbance band at about 390 nm.

Figure 4:
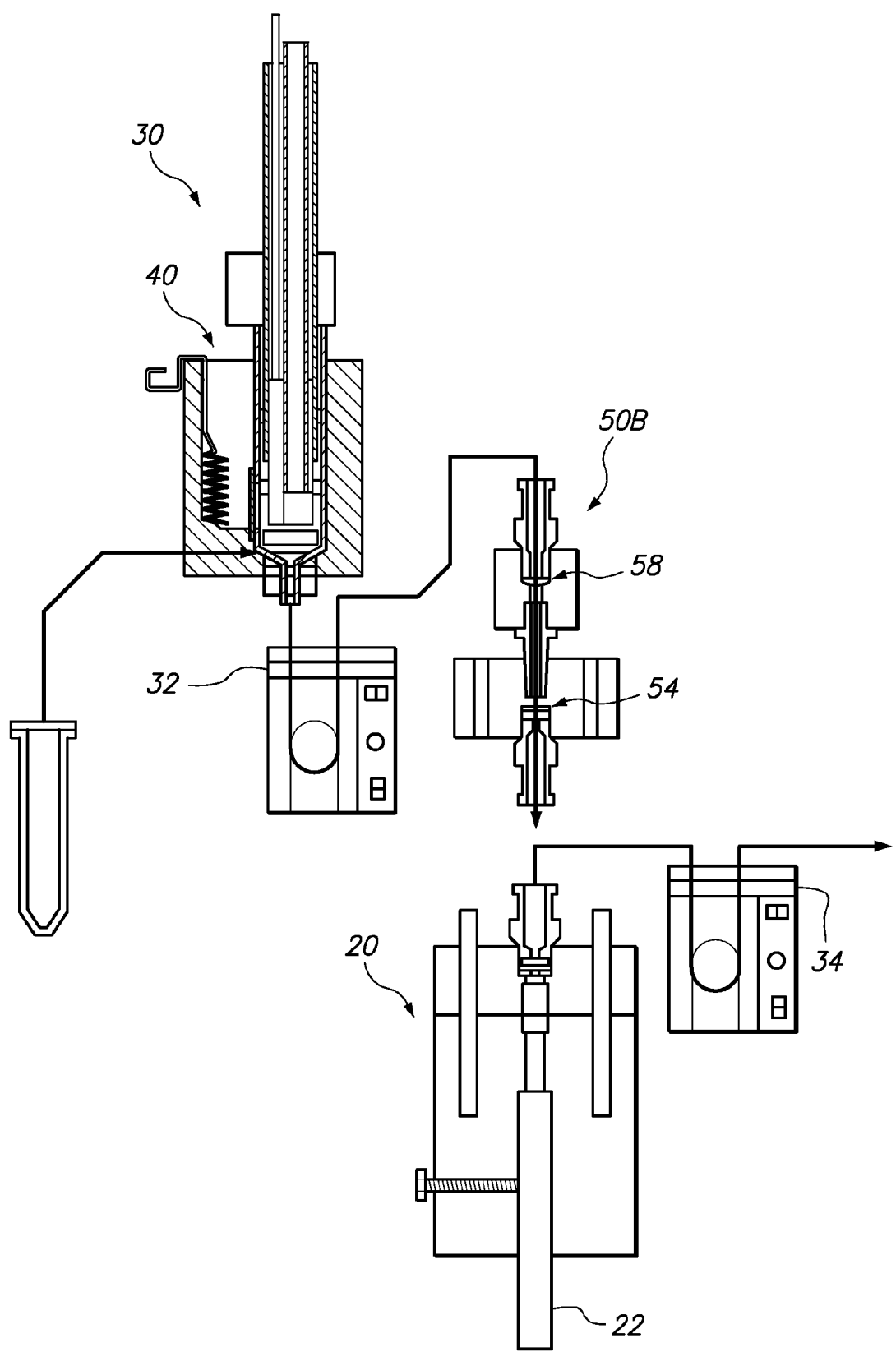
FIG. 4 is a diagram of a complete system for determining the amount of an iodine-containing organic compound.

FIG. 4 is a schematic diagram of a complete Iothalamate determination system 30 using a two electrode system for electrochemical dissociation of Iothalamate. This fully operational system for the determination of Iothalamate in plasma includes: (1) a two electrode/two compartment electrochemical cell 40 for the dissociation of Iothalamate, (2) an oxidation and exposure system 50B including a glass filter membrane 58 loaded with Oxone for oxidation of released iodide to iodine and a PVP coated membrane 54 for capturing iodine as iodine-PVP complex, and (4) the optical detection system 20 including the fiber optic probe 22 connected to a light source and spectrophotometer (not shown) for quantification of the iodine-PVP complex by reflectance absorbance spectroscopy. Peristaltic pumps 32, 34 are used to move fluids through the system.

In order to avoid cleaning the working electrode, prevent cross-contamination, and eliminate the errors introduced as the result of variations in the working electrode, it is preferably to utilize a single-use disposable electrode. Such an electrode may be made from commercially available screen printed carbon electrodes prepared in the desired shape and size using a semiautomatic screen printer (such as Model SPM, Speedline Technologies) using carbon ink from Acheson or Ercon. The screen printed carbon electrodes are then modified with bismuth to have a high over-potential for hydrogen reduction.

For example, to prepare a working electrode, the bismuth film can be electrodeposited over a screen printed carbon electrode by immersing the electrode in a non-deaerated and stirred bismuth plating solution [100 mg/L Bi(III) in an acetate buffer (0.1 M, pH 4.5) medium] and applying a potential of −0.8V (vs. a Ag/AgCl reference electrode) for 4 minutes. The bismuth-coated electrode is preferably then rinsed carefully with deionized water. In a further example, a counter electrode may be made using a screen printed carbon electrode and other inexpensive electrode materials that can be used to replace the platinum counter electrode. Such disposable electrodes, as well as other disposable components of the system, may be incorporated into a one-time-use cartridge based unit, where the components that come into contact with a sample fluid are discarded after use.

In embodiments involving urine samples, urea is readily oxidized by Oxone and may be present in such high concentrations that the urea consumes a significant amount of the Oxone. Optionally, the amount of Oxone available for oxidation is increased so that urea present in urine samples can be oxidized while leaving enough Oxone in order to oxidize iodide to iodine. Still, it is desirable to avoid using an excess of Oxone that will never be reacted.

Furthermore, the systems and methods of the invention should be calibrated, such as using a two point standard addition method or a look up table. Calibration with standard solutions should be performed periodically to confirm that the system is working properly.

Example 1

Preparation of Oxidation Filters and Chemical Oxidation of Iodide to Iodine

Figures 5A, 5B:
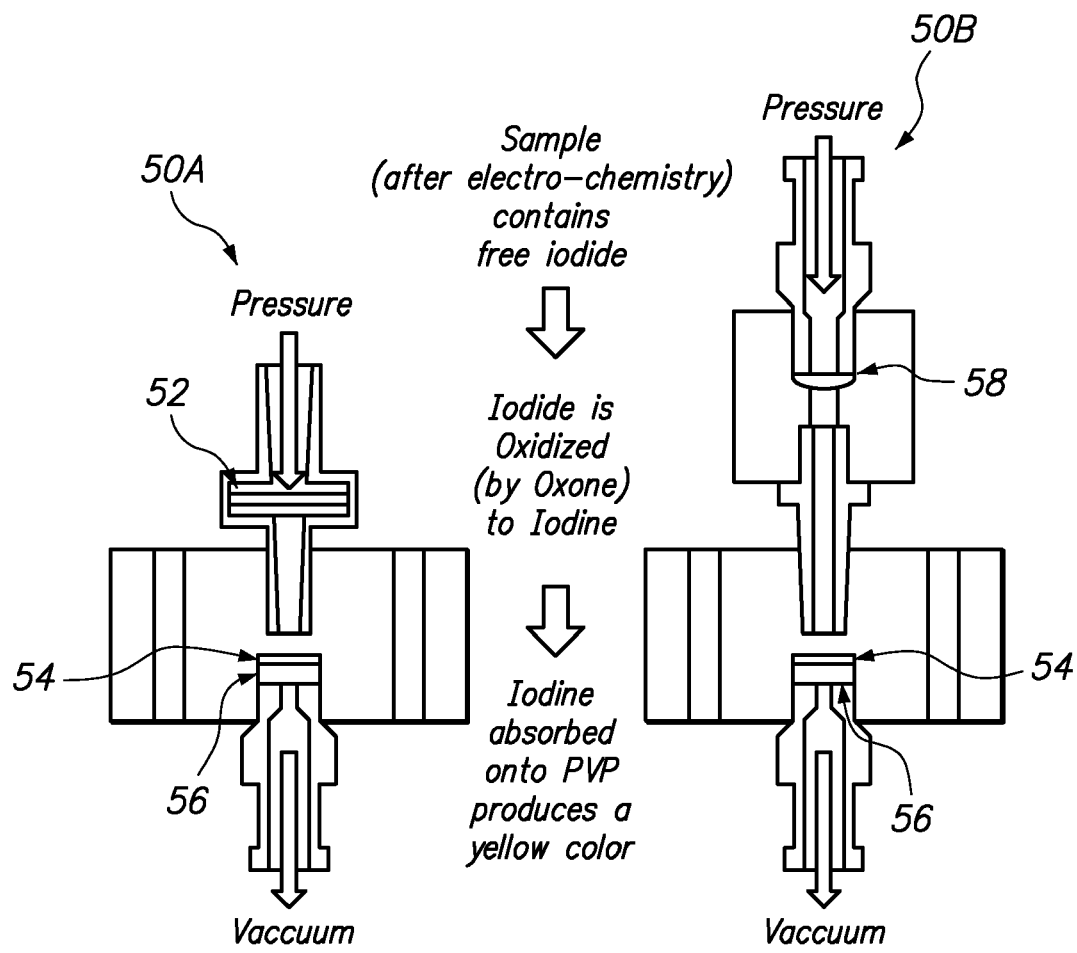
FIG. 5 is a diagram of two different versions of an assembly combining an iodide oxidation system and part of a molecular iodine measuring system that includes a PVP membrane for absorption of iodine.

A first oxidation and PVP exposure system 50A was assembled as shown in FIG. 5A. The system included a PTFE filter 52 having a 0.45 mm pore size and a diameter of 13 mm for supporting dried Oxone, a second filter 54 coated with polyvinyl pyrrolidone (PVP), and a porous frit 56 (10 μm UHMWPE, diameter 0.188 inches, thickness 0.062 inches). 40 μL of 2 mg/mL of aqueous Oxone solution was placed into the 13 mm hydrophilic PTFE syringe filter 52 and the iodide-containing sample was flowed through it. It was found that allowing the Oxone to dry for a period of several hours increased the capacity to oxidize iodide in a subsequent sample. It is believed that the dried Oxone takes some time to re-dissolve, and thus remains a bit longer in the syringe filter and becomes available to a larger fraction of the aqueous iodide sample flowing through the syringe filter.

In a similar run using the system 50B shown in FIG. 5B, the Oxone solution was also flowed through a glass filter membrane (Whatman: 934 AH), instead of the syringe filter, and allowed to dry overnight. Once dry, the glass filter membrane with Oxone was cut into small circles 58 (about 6 mm in diameter), placed in a plastic holder, and used in place of the commercial 13 mm syringe filter. Use of the glass filter membrane with Oxone significantly reduced the run to run variations, such that the sample to sample reproducibility of the entire system was within +/−10% (often within +/−5%).

Figure 6:
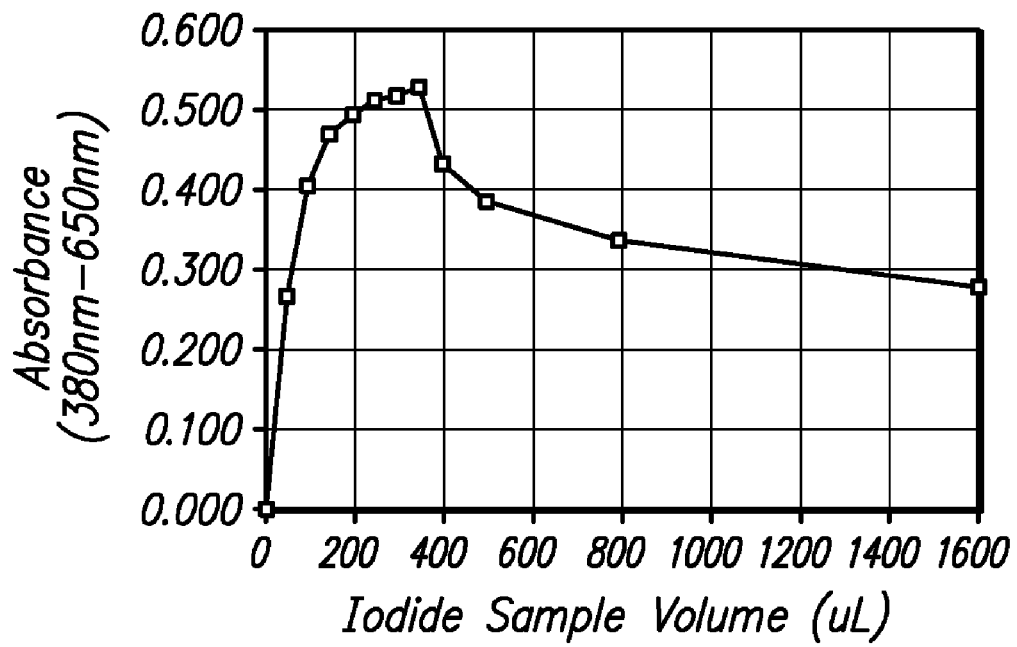
FIG. 6 is a graph of absorbance as a function of iodide sample volume showing an optimum sample size.

FIG. 6 is a graph showing that the quantity of an iodide-containing sample passed through the oxidation and PVP systems affected the measured amount of light absorbance. As sample volume increases, the absorbance increases as Iodide is being oxidized to iodine. However, if the Oxone is either consumed or washed away, further sample flow only served to wash away the iodine-PVP complex that was previously formed on the sensing membrane. A sample size of 200 μL was found to be effective and was used for all the experiments performed afterward.

Example 2

Electrolysis Parameters

Figure 7:
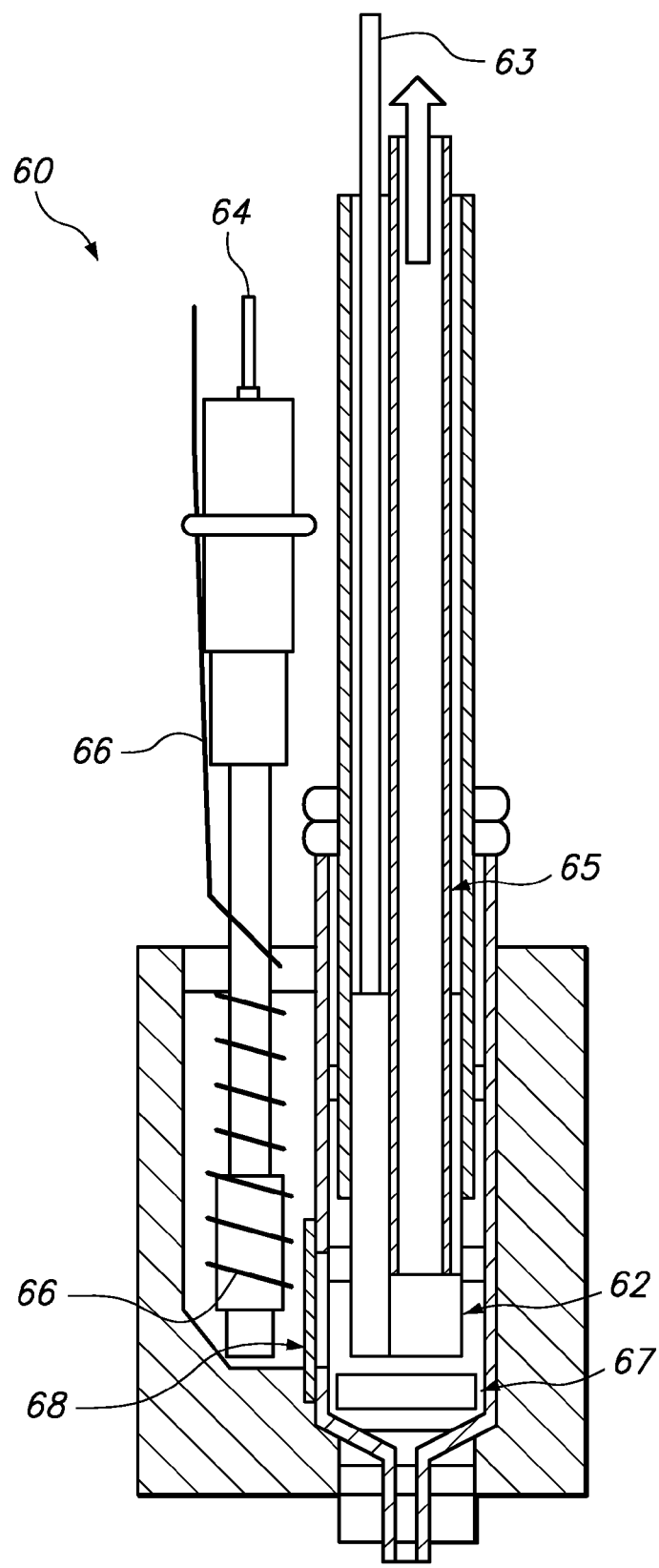
FIG. 7 is a diagram of a simplified two electrode, two compartment cell for electrolysis of an iodine-containing organic compound, such as Iothalamate.

Referring to FIG. 7, a three electrode system cell 60 with a potentiostat from CH Instruments Model 730A (not shown) was used for the optimization of the electrochemical cell and the parameters for the electrolysis of Iothalamate in pH 7.4 phosphate buffer saline 0.1M in phosphate with 0.15 M NaCl (PBS). An in-house fabricated bismuth electrode 62 (as described above), a commercial Ag/AgCl electrode 64 and a platinum coil 66 served as the working, reference and counter electrodes, respectively in the three electrode electrolysis cell with two compartments separated by a Nafion membrane 68. The bismuth electrode 62 is coupled to a contact wire 63 for connection to the potentiostat. A glass vent tube 65 allows gasses and foam to escape the cell.

The bismuth electrode was placed in the cathode compartment and the Ag/AgCl reference and platinum coil counter electrodes were placed in the anode compartment. The anode compartment was filled with half 4% perchloric acid and half PBS. The sample solution (500 μL 4% perchloric acid+500 μL 50 ppm Iothalamate in pH 7.4 PBS) was placed in the cathode compartment with the bismuth electrode and stirred with a magnetic stirrer 67 during electrolysis. Perchloric acid is used for removal of protein from both plasma and urine samples by precipitation. In addition, perchloric acid also functions as the supporting electrolyte and provides suitable conditions for electrochemical dissociation of Iothalamate. Once the optimal potential (−1.6 V vs. Ag/AgCl) for electrolysis of Iothalamate in PBS was determined, Iothalamate samples containing 4% bovine serum albumin (BSA) were tested as a substitute for human plasma. However, each sample containing BSA was centrifuged after mixing with perchloric acid to remove the precipitated proteins prior to placing the sample into the electrochemical cell. Otherwise, the proteins tend to cause foaming and clogging of the oxidizer filter.

Example 3

Electrolysis in a Two Electrode System

Figure 8:
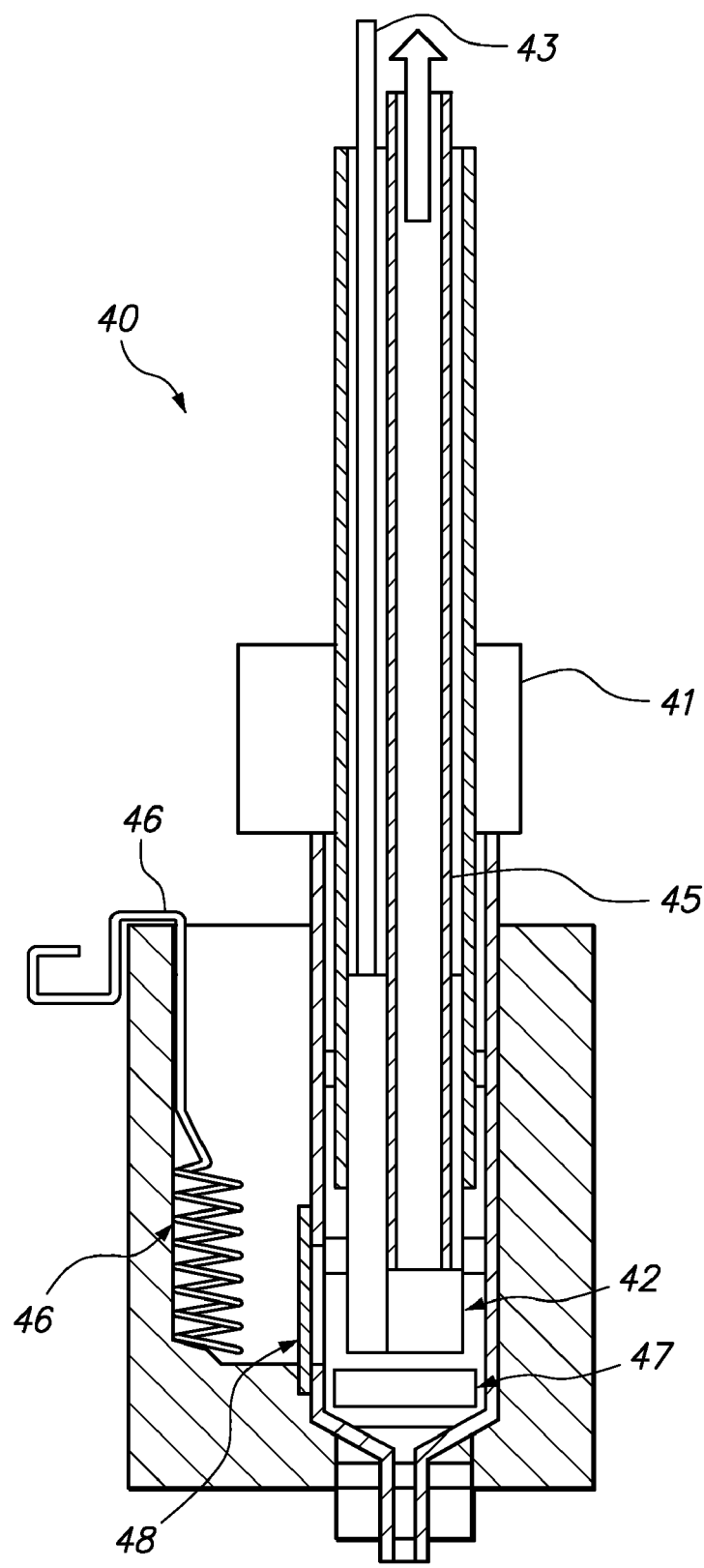
FIG. 8 is a diagram of a three electrode, two compartment cell for electrolysis of an iodine-containing organic compound, such as Iothalamate.

The electrochemical cell may be simplified by changing from a three electrode system and a potentiostat (of FIG. 7), to the two electrode system 40 (of FIG. 8) having a constant voltage power supply (not shown). The voltages and currents across the bismuth electrode 42 and the platinum coil counter electrode 46 under the optimized electrolysis conditions were monitored using a multi-meter in the three electrode system. The voltage measured across the bismuth working electrode and the platinum coil counter electrode during the electrolysis of Iothalamate using the potentiostat was then used as the starting potential in the experiments performed in the two electrode electrolysis system 40 (FIG. 8). As voltage is increased, the chemical reaction rate increases, but so does the rate of foam generation due to generation of hydrogen gas. The maximum voltage that was used across the bismuth working electrode 42 and the platinum coil counter electrode 46, while still generating only a minimal amount of foam, was −3.6V.

The system 40 is secured with a support bracket 41. A Nafion membrane 48 separates the chamber into two compartments. A micro-stir bar 47 is provided for use during the electrolysis. Gas and foam generated during the electrolysis are allowed to escape through the glass vent tube 45.

Example 4

Electrolysis Duration

Figure 9:
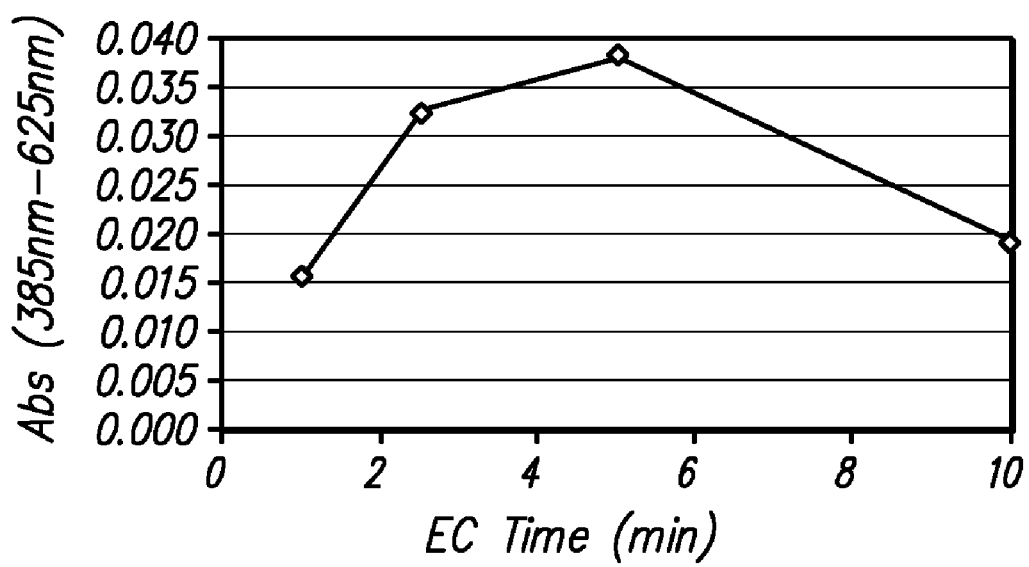
FIG. 9 is a graph of absorbance as a function of electrolysis time.

The optimal duration of electrolysis was investigated by electrolyzing 50 ppm Iothalamate in 4% BSA in pH 7.4 PBS at −3.6 V in the two electrode two compartment cell for 1, 2, 5 and 10 minutes. The results presented in FIG. 9 show an increase in the signal (absorbance due to iodine-PVP complex formation) increase with increase in electrolysis time. Based upon these results a 5 minute electrolysis time was determined to be optimal and used for all further experiments.

Example 5

Process for Determining the Amount of Iothalamate in Solution

Figure 10:
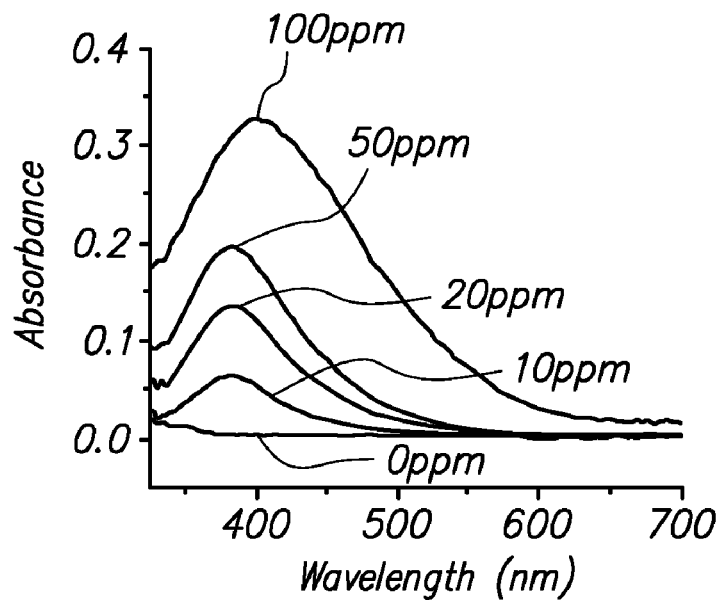
FIG. 10 is a graph of reflectance absorbance spectra obtained for 4% BSA samples spiked with 0, 10, 20, 50 and 100 ppm Iothalamate.
Figure 11:
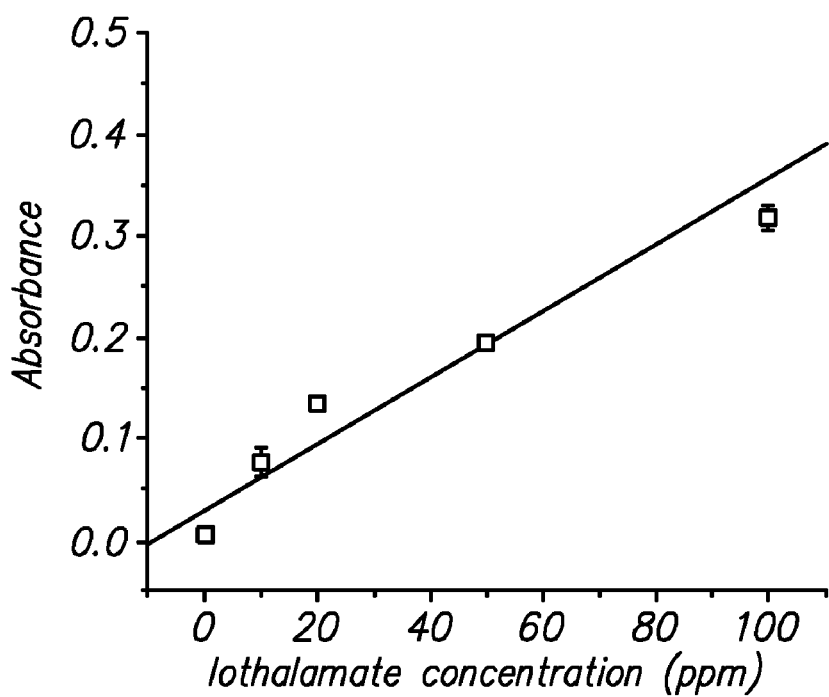
FIG. 11 is a graph of a standard curve for Iothalamate in 4% BSA created from average of triplicate runs.

A solution of 4% bovine serum albumin (BSA) in pH 7.4 PBS was used as a substitute for human plasma during the optimization of the entire Iothalamate detection system. A set of reflectance absorbance spectra obtained for 4% BSA spiked with 0, 10, 20, 50 and 100 ppm of Iothalamate is presented in FIG. 10. The Standard curve prepared for Iothalamate in 4% BSA, presented in FIG. 11, was obtained by running triplicates of 4% BSA samples spiked with 0-100 ppm of Iothalamate as described in the block diagram in FIG. 12. Even though the standard curve is not perfectly linear over the entire range (0-100 ppm), this result demonstrates the applicability of this technology for Iothalamate determination as the error bars are relatively small.

Figure 12:
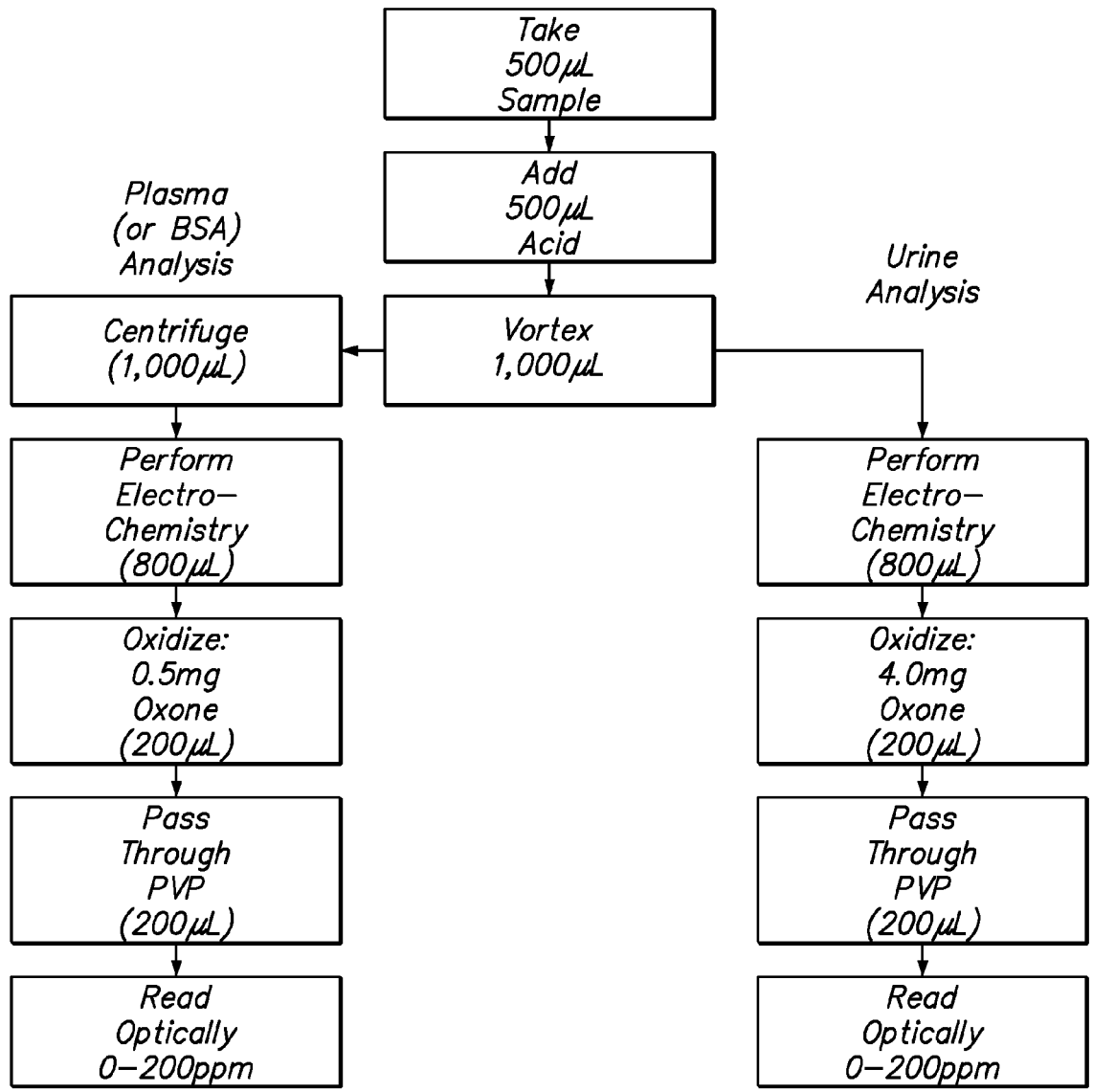
FIG. 12 is a flow chart showing the sequence of steps performed during analysis of plasma/BSA or urine samples.

The optimized Iothalamate determination system may be described by a block diagram of the basic process steps as shown in FIG. 12. The block diagram shows two parallel processes in which Plasma and Urine analysis requirements are slightly different. Precipitates formed when plasma or BSA are mixed with perchloric acid must be removed by centrifugation. Secondly, urine analysis requires 4-8 times more Oxone (as iodide is not oxidized until all of the urea present in the urine sample is oxidized) than does Plasma/BSA analysis. However, other than these two discrepancies, the processes may be identical. The absorbance values obtained from the tests performed with various concentrations of iodide in pH 7.4 PBS were compared to the absorbance values obtained from the 4% BSA sample and confirm that the electrolysis process is quantitative (FIG. 13).

Figure 13:
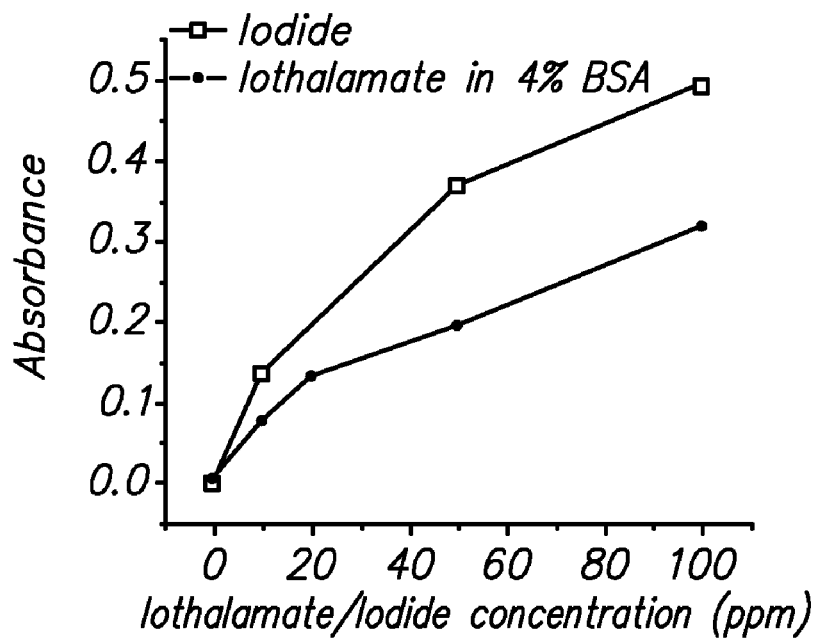
FIG. 13 is a graph of the absorbance values for Iothalamate in BSA and for iodide.

As shown in FIG. 13, the absorbance values obtained for the various concentrations of Iothalamate (Iothalamate meglumine) compared to the corresponding concentrations of iodide are about half. Since, approximately half of the mass of Iothalamate meglumine consists of iodine, this result suggests that iodide is released quantitatively from Iothalamate by the electrochemical process.

Example 6

Determination of Iothalamate in Plasma

Iothalamate concentrations in human plasma samples spiked with Iothalamate were successfully determined using the parameters optimized for determination of Iothalamate in 4% BSA as summarized in FIG. 12.

Figure 14:
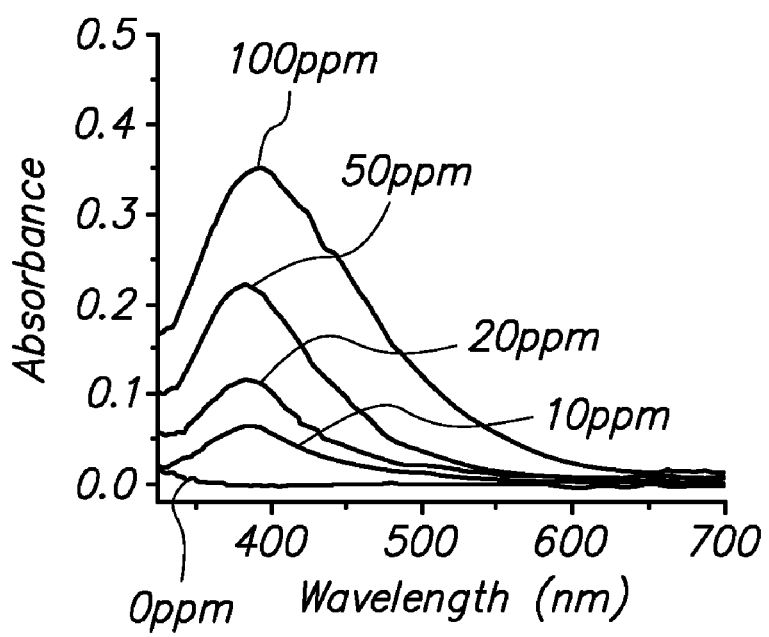
FIG. 14 is a graph of reflectance absorbance spectra obtained for human plasma samples spiked with 0, 10, 20, 50 and 100 ppm Iothalamate.

In brief, 500 μL of plasma sample and 500 μL of 4% perchloric acid are taken in a centrifuge tube, vortexed to mix, then centrifuged at 15,000 rpm for 1 minute to separate the precipitated proteins. 800 μL of the clear supernatant solution is then pipetted into the sample compartment of the two compartment electrochemical cell. A platinum coil electrode is placed into the other compartment separated by Nafion membrane and is filled with a 1:1 mixture of 4% perchloric acid and pH 7.4 PBS. The bismuth electrode is cleaned and placed into the sample compartment, the sample solution is stirred using a magnetic stirrer, then −3.6 V is applied (using a regulated power supply) to the bismuth electrode for 5 minutes. 200 μL of the electrolyzed solution is then passed first through the glass microfiber filter loaded with 0.5 mg of Oxone, and second through the PVP coated membrane. The amount of Iothalamate present in the sample was then determined from the absorbance due to the iodine-PVP complex in the reflectance absorbance spectrum. A set of reflectance absorbance spectra for human plasma samples spiked with 0, 10, 20, 50 and 100 ppm of Iothalamate meglumine is presented in FIG. 14.

Figure 15:
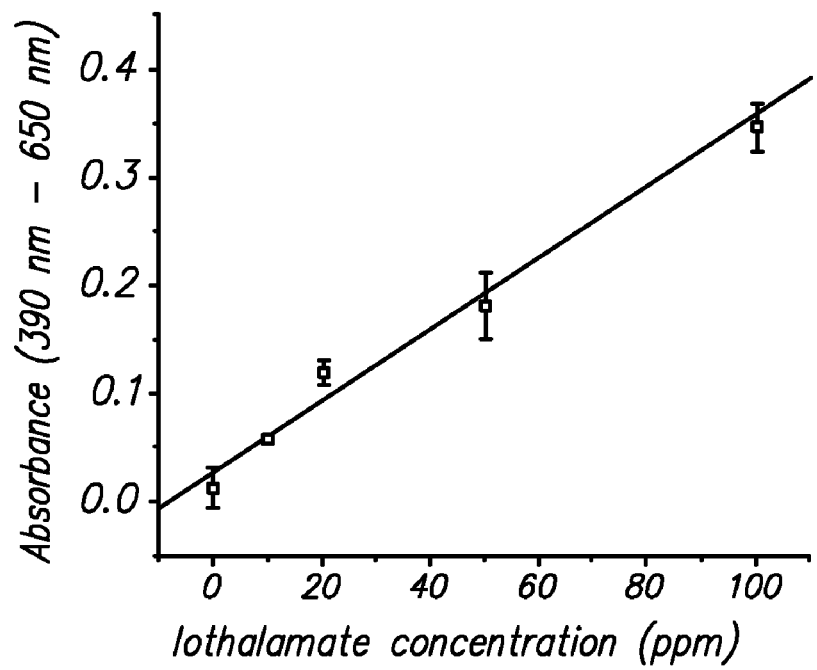
FIG. 15 is a graph of a standard curve for Iothalamate in human plasma.

The average values of absorbance at 390 nm were corrected for baseline drift by subtracting the absorbance at 650 nm from three sets of such experiments and are plotted against the Iothalamate concentration in FIG. 15 to construct a standard curve. The standard curve for Iothalamate in plasma for the five different concentrations (0-100 ppm) demonstrated a correlation coefficient of 0.981 with an intercept close to zero (0.026 ppm).

Example 7

Determination of Iothalamate in Urine

Figure 16:
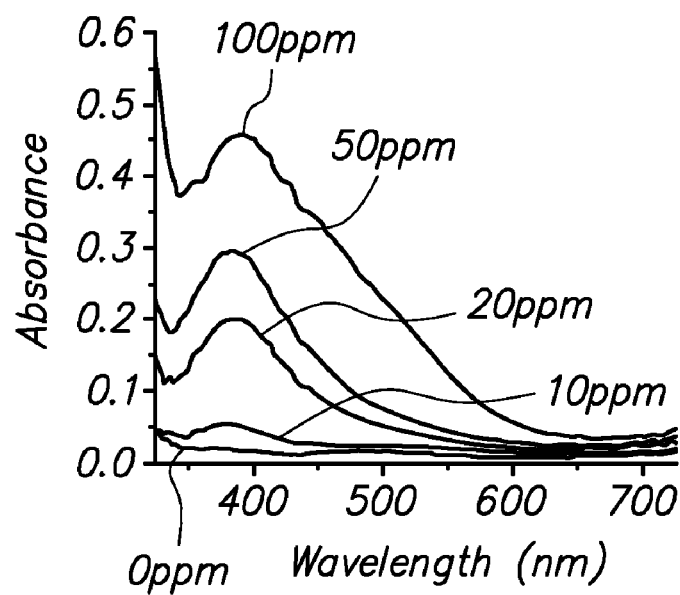
FIG. 16 is a graph of reflectance absorbance spectra obtained for urine samples spiked with 0, 10, 20, 50 and 100 ppm Iothalamate.

The urine samples did not require centrifugation because they had a negligible amount of protein compared to the plasma samples. However, urine samples spiked with Iothalamate failed to develop any color when tested under the conditions optimized for 4% BSA and plasma samples. It was determined that the oxidizer (0.5 mg of Oxone loaded in the glass microfiber filter) was completely consumed by the urea present in the urine sample and the iodide generated from the dissociation of Iothalamate was not being oxidized to iodine. The problem of oxidizer consumption was overcome by increasing the amount of Oxone loaded onto the glass microfiber filter. Iothalamate in urine samples was successfully determined as in plasma samples by using 2 mg or more Oxone per sample. We chose to use 4 mg of Oxone per sample to make sure that enough oxidizer was always available for oxidation of iodide to iodine. A set of reflectance absorbance spectra obtained for urine samples spiked with 0, 10, 20, 50 and 100 ppm Iothalamate are presented in FIG. 16.

Figure 17:
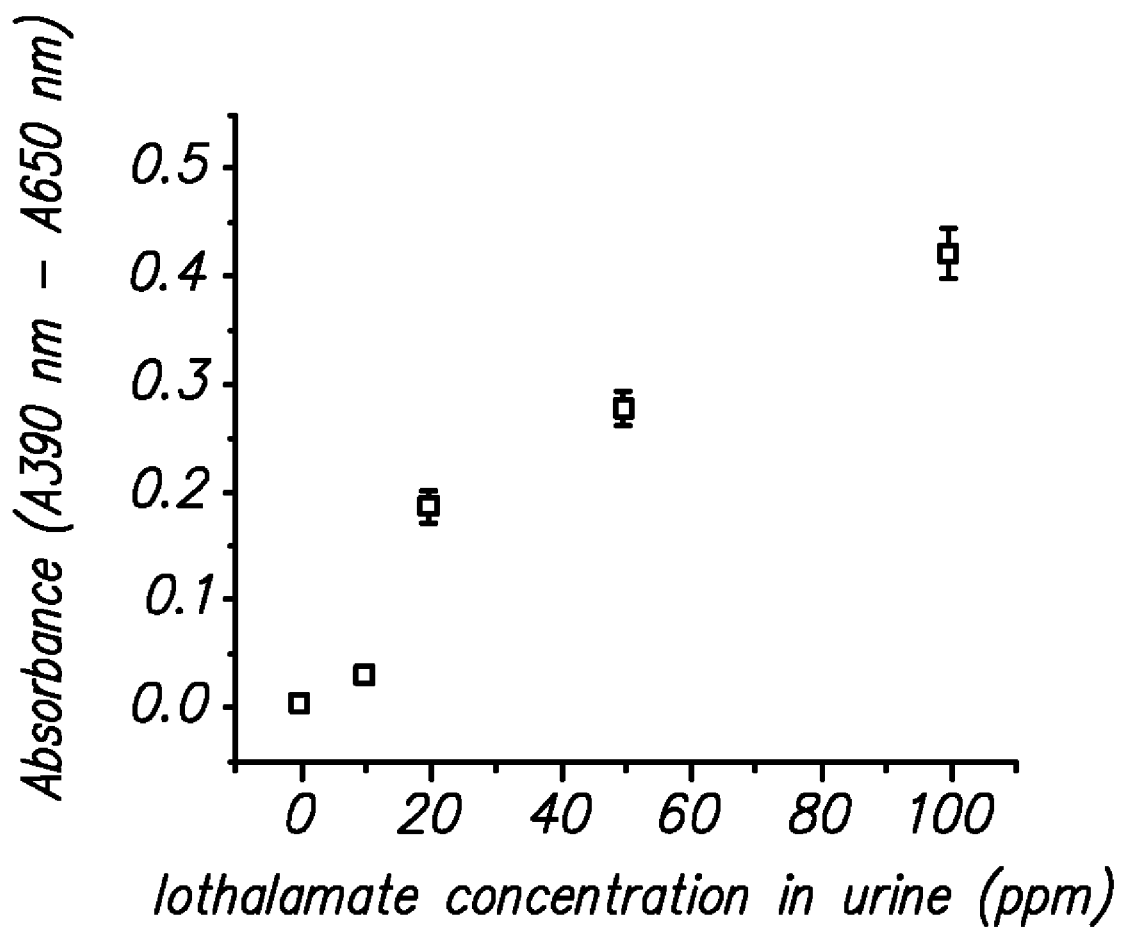
FIG. 17 is a graph of a standard curve for Iothalamate in urine.

The average values of absorbance at 390 nm were corrected for baseline drift from three sets of such experiments and plotted against the Iothalamate concentration in FIG. 17. Even though the calibration curve obtained for Iothalamate in urine is not as linear as that for Iothalamate in plasma, because of the high degree of reproducibility/small error bars it can still be used for accurate determination of Iothalamate in urine samples with less than 10% relative error.

The terms "comprising," "including," and "having," as used in the claims and specification herein, shall be considered as indicating an open group that may include other elements not specified. The term "consisting essentially of," as used in the claims and specification herein, shall be considered as indicating a partially open group that may include other elements not specified, so long as those other elements do not materially alter the basic and novel characteristics of the claimed invention. The terms "a," "an," and the singular forms of words shall be taken to include the plural form of the same words, such that the terms mean that one or more of something is provided. The terms "at least one" and "one or more" are used interchangeably. The term "one" or "single" shall be used to indicate that one and only one of something is intended. Similarly, other specific integer values, such as "two," are used when a specific number of things is intended. The terms "preferably," "preferred," "prefer," "optionally," "may," and similar terms are used to indicate that an item, condition or step being referred to is an optional (not required) feature of the invention.

What is claimed is:

1. A method of determining the amount of a known iodine-containing organic compound in an aqueous solution, comprising:
    electrochemically reducing the known iodine-containing organic compound in an aqueous medium to release iodide anions, wherein the iodine-containing organic compound is reduced in an electrochemical cell including a working electrode separated from a counter electrode by a cation exchange membrane; and wherein the working electrode is a mercury working electrode or a bismuth working electrode;
    chemically oxidizing the iodide anions to produce molecular iodine; and
    measuring the amount of molecular iodine.

2. The method of claim 1, wherein the step of measuring the amount of iodine comprises:
    extracting the iodine on a polyvinylpyrrolidone coated membrane to form an iodine-PVP complex; and
    measuring the color of the iodine-PVP complex on the coated membrane.

3. The method of claim 2, wherein the polyvinylpyrrolidone is coated on one side of the coated membrane.

4. The method of claim 2, wherein the coated membrane includes poly(styrenedivinylbenzene).

5. The method of claim 2, wherein step of measuring the color of the iodine-PVP complex includes a reflectance absorbance measurement.

6. The method of claim 2, wherein step of measuring the color of the iodine-PVP complex is performed using a spectrophotometer.

7. The method of claim 6, wherein the spectrophotometer is coupled to an optical fiber probe including at least one illumination fiber and at least one read fiber.

8. The method of claim 1, wherein the aqueous solution includes plasma or urine.

9. The method of claim 1, wherein the known iodine-containing organic compound is an aryl iodide.

10. The method of claim 9, wherein the aryl iodide is a glomerular filtration rate marker compound.

11. The method of claim 9, wherein the aryl iodide is an Iothalamate.

12. The method of claim 11, wherein the Iothalamate is Iothalamate meglumine.

13. The method of claim 1, wherein the iodide anions are chemically oxidized with an oxidizing agent selected from the group consisting of peroxymonosulfate, ozone, and combinations thereof.

14. The method of claim 1, wherein the step of measuring the amount of iodine includes a step selected from the group consisting of adding starch into the iodine solution, adding leucocrystal violet into the iodine solution, measuring the direct ultraviolet absorption of iodine, and titrating the iodine with sodium thio sulfate.

15. The method of claim 1, wherein the aqueous solution contains protein, the method further comprising:
    removing a majority of the protein from the aqueous solution prior to electrochemically reducing the known iodine-containing organic compound.

16. The method of claim 15, wherein the aqueous solution includes a body fluid from an animal.

17. The method of claim 16, wherein the body fluid is selected from the group consisting of plasma and urine.

18. The method of claim 1, further comprising:
    administering the iodine-containing organic compound into the body of an animal;

periodically obtaining a sample the blood or urine of the animal during the period following administration of the iodine-containing organic compound;

repeating the steps of claim 1 for each sample obtained; and using the quantity of iodide determined for each sample to determine a glomerular filtration rate for the animal.

19. The method of claim 1, further comprising:

measuring the background amount of iodide found in the plasma or urine; and subtracting the background amount of iodide from the measured amount of iodine to obtain the amount of the iodine dissociated from the iodine-containing organic compound.

20. The method of claim 1, wherein the working electrode is a bismuth-modified electrode.

21. The method of claim 20, wherein the bismuth-modified electrode is selected from the group consisting of bismuth-modified gold, bismuth-modified carbon, and combinations thereof.

22. The method of claim 1, wherein the working electrode includes mercury.

23. The method of claim 1, wherein the counter electrode is a platinum electrode.

24. The method of claim 1, wherein the step of chemically oxidizing the iodide anions includes passing the aqueous medium with the released iodide anions through a filter pre-loaded with a powdered oxidant.

25. The method of claim 24, wherein the powdered oxidant is peroxymonosulfate.

26. The method of claim 1, wherein the step of chemically oxidizing the iodide anions includes mixing an oxidant into the aqueous medium with the released iodide anions.

27. The method of claim 1, wherein the step of chemically oxidizing the iodide anions is performed in an airtight reaction vessel.

* * * * *